United States Patent
Lee

(10) Patent No.: US 10,172,330 B2
(45) Date of Patent: Jan. 8, 2019

(54) GAS SENSING DEVICE

(71) Applicant: ECinU Co., Ltd., Daegu (KR)

(72) Inventor: Sin-Woo Lee, Daegu (KR)

(73) Assignee: ECinU Co., Ltd., Daegu (KR)

( * ) Notice: Subject to any disclaimer, the term of this patent is extended or adjusted under 35 U.S.C. 154(b) by 236 days.

(21) Appl. No.: 15/300,035

(22) PCT Filed: Jul. 28, 2015

(86) PCT No.: PCT/KR2015/007896
§ 371 (c)(1),
(2) Date: Sep. 28, 2016

(87) PCT Pub. No.: WO2016/148353
PCT Pub. Date: Sep. 22, 2016

(65) Prior Publication Data
US 2017/0172115 A1 Jun. 22, 2017

(30) Foreign Application Priority Data
Mar. 13, 2015 (KR) .......................... 10-2015-0034775

(51) Int. Cl.
*A01K 63/00* (2017.01)
*A01K 63/04* (2006.01)
*G01N 21/59* (2006.01)
*A01G 7/02* (2006.01)

(52) U.S. Cl.
CPC .............. *A01K 63/006* (2013.01); *A01G 7/02* (2013.01); *A01K 63/042* (2013.01); *G01N 21/59* (2013.01)

(58) Field of Classification Search
CPC ...... A01K 63/006; A01K 63/042; A01G 7/02; G01N 21/59

USPC ............................................................. 137/2
See application file for complete search history.

(56) References Cited

U.S. PATENT DOCUMENTS

| | | | | |
|---|---|---|---|---|
| 4,072,612 A | * | 2/1978 | Daniel ................. | A01K 63/042 210/167.23 |
| 4,859,864 A | * | 8/1989 | Smith ................... | A61M 5/365 250/577 |
| 5,582,777 A | * | 12/1996 | Vento ................... | A01K 63/042 261/121.2 |

FOREIGN PATENT DOCUMENTS

| | | |
|---|---|---|
| JP | 08-308432 A | 11/1996 |
| JP | 2002-177953 A | 6/2002 |
| JP | 2013-078274 A | 5/2013 |
| KR | 10-2011-0126258 A | 11/2011 |

(Continued)

*Primary Examiner* — P. Macade Nichols
(74) *Attorney, Agent, or Firm* — Novick, Kim & Lee, PLLC; Jae Youn Kim

(57) ABSTRACT

The present invention relates to an apparatus for sensing and controlling an amount of gas supply and a method for sensing and controlling an amount of gas supply thereby, which can sense a supply amount of the corresponding gas from an optical sensor in real time on the basis of the number of bubbles generated by any set time difference at the time when a target gas flows in a tube in order to differentiate the supply amount more accurately and whether or not the gas supply state is bad, and which can control pressure of the tube in real time by a series of automated devices in order to precisely realize the target supply amount according to gas supply information obtained from the optical sensor, thereby positively preventing malfunction and continuously maintaining the initial set amount of gas supply.

3 Claims, 4 Drawing Sheets

(56) References Cited

FOREIGN PATENT DOCUMENTS

KR 10-2012-0013675 A 2/2012
KR 10-1188232 B1 10/2012

* cited by examiner

GAS SENSING DEVICE

TECHNICAL FIELD

The present invention relates to an apparatus for sensing and controlling an amount of gas supply and a method for sensing and controlling an amount of gas supply thereby, which can sense a supply amount of the corresponding gas from an optical sensor in real time on the basis of the number of bubbles generated by any set time difference at the time when a target gas flows in a tube in order to differentiate the supply amount more accurately and whether or not the gas supply state is bad, and which can control pressure of the tube in real time by a series of automated devices in order to precisely realize the target supply amount according to gas supply information obtained from the optical sensor, thereby positively preventing malfunction and continuously maintaining the initial set amount of gas supply.

BACKGROUND ART

Recently, the number of people who breed aquarium fishes and water plants in large and small aquariums at home and shops is growing.

Because aquarium fishes in aquariums move dynamically and have beautiful colors and shapes, if such aquariums are installed in houses or shops, it provides an interior decoration effect. Therefore, the number of people who install aquariums is increasing.

In order to raise aquarium fishes in aquariums in which water plants are put, an adequate amount of carbon dioxide must be put in the aquarium so as to grow the water plants normally.

For instance, Korean Patent No. 1,188,232 discloses a "carbon dioxide supply device for aquarium" which can supply an adequate amount of carbon dioxide into an aquarium.

The conventional carbon dioxide supply device has the structure that a valve capable of being adjusted by a user is mounted at an outlet of a gas barrel, in which carbon dioxide is compressed and stored, so that carbon dioxide is supplied into the aquarium through a supply hose according to opening and closing of the valve.

However, all prior arts as well as the above-mentioned conventional carbon dioxide supply device have a huge problem in operation because they have no means for showing a supply state in real time when carbon dioxide is supplied.

In other words, although the supply amount of carbon dioxide is changed suddenly by internal situations or external factors of the aquarium, such prior arts cannot allow users to realize immediately. Additionally, because the prior arts do not have any means for properly controlling the supply amount according to all situations, people demand more effective systems for solving the above problems.

Technical Problem

Accordingly, the present invention has been made in an effort to solve the above-mentioned problems occurring in the prior arts, and it is an object of the present invention to provide an apparatus for sensing and controlling an amount of gas supply which can grasp a flow speed and a flow amount without any interruption to flowability of gas and allow a user to recognize a state change in real time to sense a flow of gas flowing from the bottom to the top through a tube when the user supplies carbon dioxide into an aquarium, and which can automatically correct the supply amount of gas to match a target supply amount of gas by a series of automated devices.

It is another object of the present invention to provide an improved and differentiated method for sensing and controlling an amount of gas supply using such an apparatus for sensing and controlling an amount of gas supply.

Technical Solution

To achieve the above objects, the present invention provides an apparatus for sensing and controlling an amount of gas supply including: a tube for allowing target gas to flow from the bottom to the top; a sensing unit engaged to the external surface of the tube to sense the number of bubbles of the target gas, which sequentially moves for a predetermined period of setting time in the inner space of the tube, in real time by applying an optical sensor based on signal information of a light emitting diode and a transistor, which are positioned to face each other; a controller for receiving the bubble information from the sensing unit to determine whether the bubble information matches the target amount of gas supply in consideration of the predetermined period of setting time; and a pressure controlling unit which is operated by a signal obtained from the controller and varies the number of bubbles during a predetermined period of time by determining the degree of a blocked state of the inner space of the tube through a motor so as to match the varied number of bubbles to the target amount of gas supply.

Here, the pressure controlling unit includes: a connector which connects the tubes with each other to provide a communicating space; a cover body joined onto the connector to fix the position of a motor; a push rod which is rotated or not rotated according to operation of the motor, has a rotational end portion with a screw thread and is fastened after vertically penetrating through a path formed from the motor to the tube; and a needle valve geared through the screw thread of the push rod and turned upside down by rotation of the push rod by the motor so as to determine the degree of opening of the inner space of the tube.

In another aspect of the present invention, the present invention provides a method for sensing and controlling an amount of gas supply includes: a first step of sensing bubbles of target gas, which flows from the bottom to the top in a tube, in real time by a sensing unit having an optical sensor; a second step of transmitting flow information of the bubbles sensed by the sensing unit to a controller in real time, and determining whether or not the flow information matches the predetermined supply amount of gas by the number of bubbles during any period of time; a third step of transmitting a command signal of the corresponding controller to a pressure controlling unit in order to vary the number of bubbles based on the determined result and match the changed number of bubbles with the target supply amount of gas; and a fourth step of rotating a push rod at an angle matching a correction value, which is reset based on the relevant information applied from the controller, so that a needle valve is turned upside down, and controlling the number of bubbles per second according to whether or not the inner space of the tube is opened or blocked.

Advantageous Effects

As described above, according to the present invention, the apparatus for sensing and controlling an amount of gas supply and the method for sensing and controlling an amount of gas supply thereby can sense the supply amount of the corresponding gas from the optical sensor in real time on the basis of the number of bubbles generated by any set time difference at the time when the target gas flows in the tube, thereby differentiating the supply amount more accurately and whether or not the gas supply state is bad.

Particularly, the apparatus for sensing and controlling an amount of gas supply and the method for sensing and controlling an amount of gas supply thereby can control pressure of the tube in real time by a series of automated devices in order to precisely realize the target supply amount according to gas supply information obtained from the optical sensor, thereby positively preventing malfunction and continuously maintaining the initial set amount of gas supply.

MODE FOR INVENTION

Hereinafter, the structure of the present invention and actions and effects by the structure of the present invention will be described in batches with reference to the attached drawings.

Advantages and features of the present invention, and method to achieve them of the present invention will be obvious with reference to embodiments along with the accompanying drawings which are described below. Meanwhile, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims. In the detailed description, the same reference numbers of the drawings refer to the same or equivalent parts of the present invention.

Figure 1:
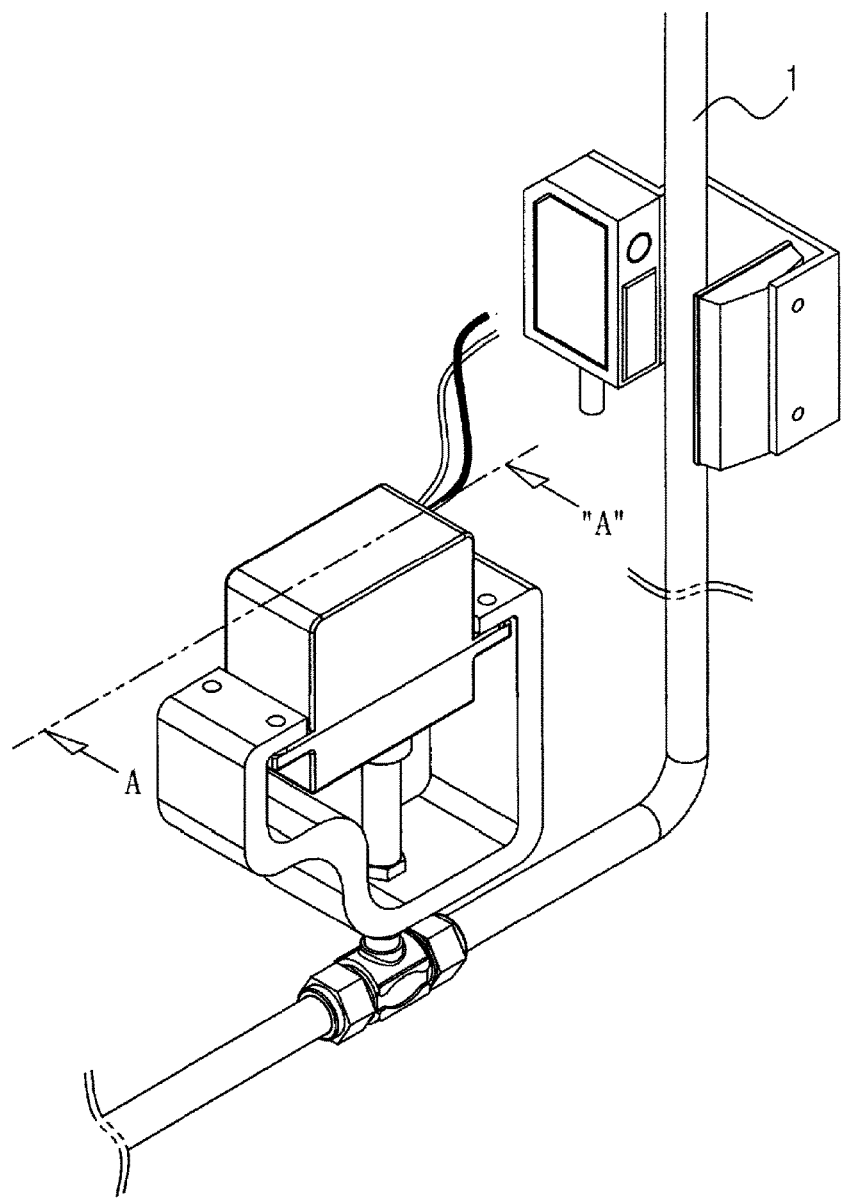
FIG. 1 is a perspective view of an apparatus for sensing and controlling an amount of gas supply according to a preferred embodiment of the present invention.
Figure 2:
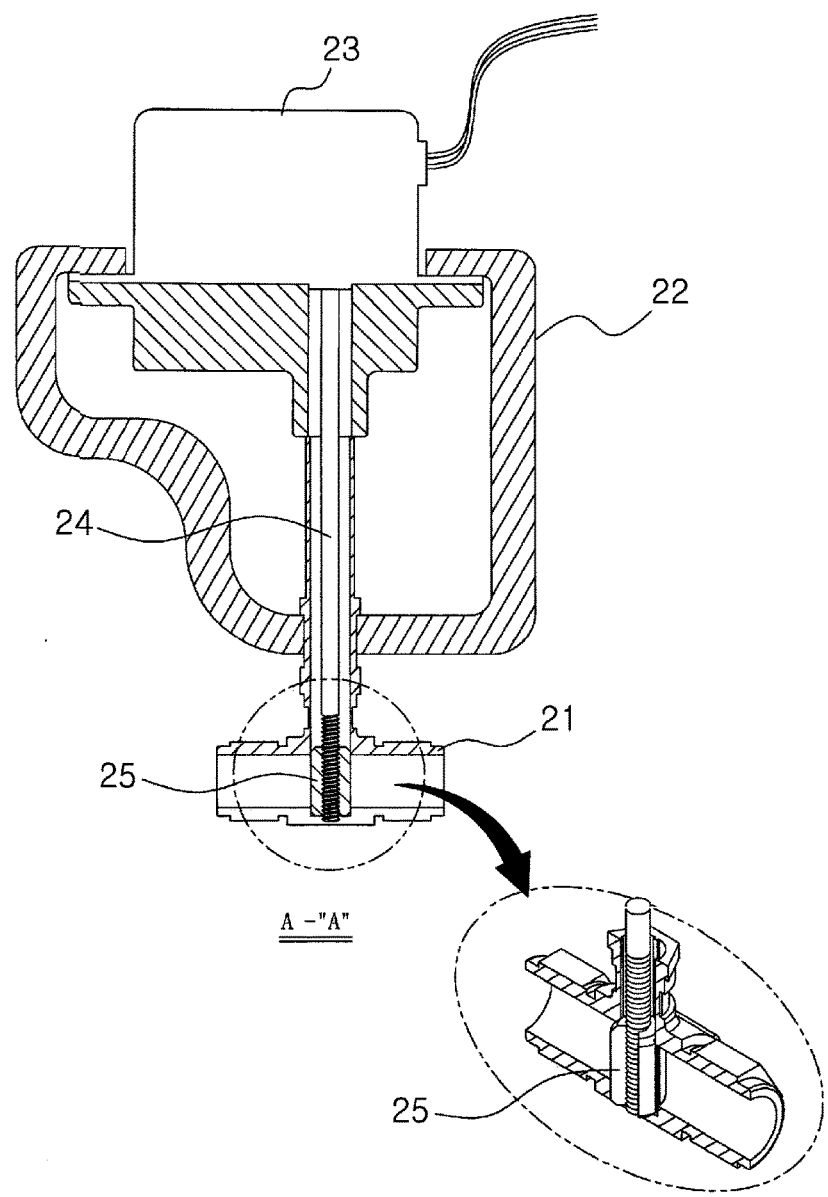
FIG. 2 is an exploded perspective view showing a pressure controlling unit, which is one of essential parts of the present invention, in detail.
Figure 3:
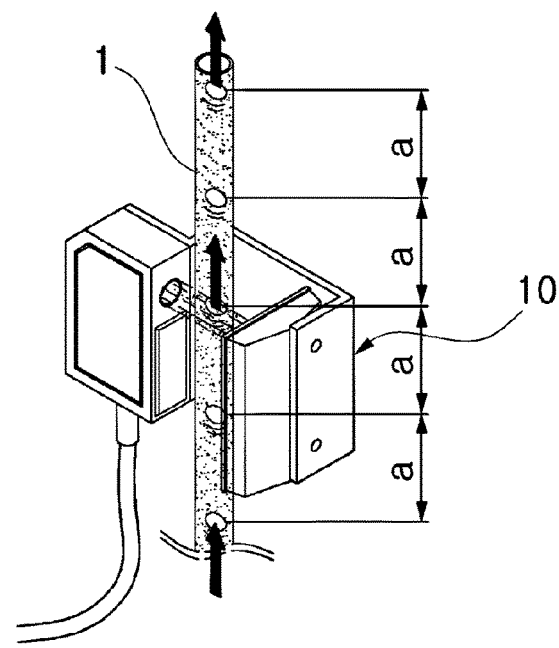
FIGS. 3 and 4 are conceptual diagrams showing examples of used states of the pressure controlling unit according to the present invention.
Figure 3:
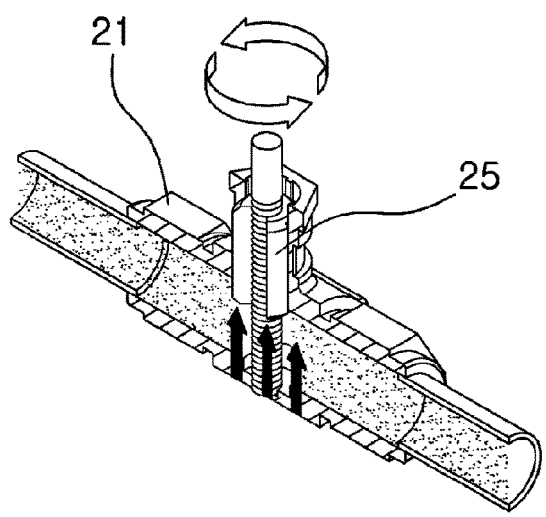
Figure 4:
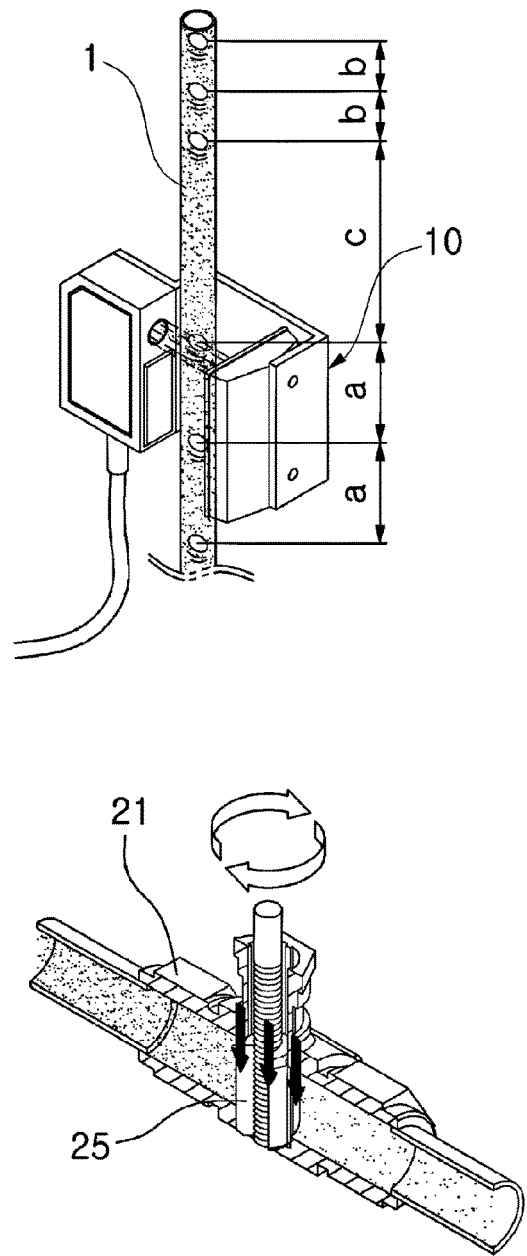

FIG. 1 is a perspective view of an apparatus for sensing and controlling an amount of gas supply according to a preferred embodiment of the present invention, FIG. 2 is an exploded perspective view showing a pressure controlling unit, which is one of essential parts of the present invention, in detail, and FIGS. 3 and 4 are conceptual diagrams showing examples of used states of the pressure controlling unit according to the present invention.

It is the main object of the present invention to obtain relevant information by a sensing unit 10 to match a target supply amount of gas, transmit the obtained information to a pressure controlling unit 20 by a controller and vary the degree of a blocked state of the inside of a tube 1 by operation of the pressure controlling unit based on the obtained information, thereby controlling the number of flows of bubbles per second.

In more detail, the present invention relates to an apparatus for sensing and controlling an amount of gas supply and a method for sensing and controlling an amount of gas supply thereby, which can sense a supply amount of the corresponding gas from an optical sensor in real time on the basis of the number of bubbles generated by any set time difference at the time when a target gas flows in a tube in order to differentiate the supply amount more accurately and whether or not the gas supply state is bad, and which can control pressure of the tube in real time by a series of automated devices in order to precisely realize the target supply amount according to gas supply information obtained from the optical sensor, thereby positively preventing malfunction and continuously maintaining the initial set amount of gas supply.

First of all, the present invention provides an apparatus 100 and a method for sensing and controlling an amount of gas supply which can grasp a flow speed and a flow amount without any interruption to flowability of gas and allow a user to recognize a state change in real time to sense a flow of gas flowing from the bottom to the top through a tube when the user supplies carbon dioxide into an aquarium, and which can automatically correct the supply amount of gas to match a target supply amount of gas by a series of automated devices.

However, all matters characterized by the present invention are applied to gas flowing from the bottom to the top and are applicable when carbon dioxide is supplied into the aquarium, and the present invention is not limited to the above but used widely.

The apparatus 100 for sensing and controlling an amount of gas supply includes: a tube 1 for allowing target gas to flow from the bottom to the top; a sensing unit 10 engaged to the external surface of the tube to sense the number of bubbles of the target gas, which sequentially moves for a predetermined period of setting time in the inner space of the tube, in real time by applying an optical sensor based on signal information of a light emitting diode and a transistor, which are positioned to face each other; a controller for receiving the bubble information from the sensing unit to determine whether the bubble information matches the target amount of gas supply in consideration of the predetermined period of setting time; and a pressure controlling unit 20 which is operated by a signal obtained from the controller and varies the number of bubbles during a predetermined period of time by determining the degree of a blocked state of the inner space of the tube through a motor so as to match the varied number of bubbles to the target amount of gas supply.

As shown in FIG. 1, the sensing unit 10 adopts the optical sensor as described above. Such an optical sensor is divided into a light transmission type optical sensor and a light reflection type optical sensor, and the present invention adopts a light transmission type optical sensor.

In other words, a light emitting diode is located at one side and a transistor is located at the other side to sense light transmitted from the light emitting diode so as to positively sense a flow of target bubbles flowing inside the tube 1.

In detail, the flow of gas inside the tube 1 can be generally recognized from the outside due to generation of bubbles, so that the user can recognize a flow amount or a supply amount of gas in real time if the number of bubbles flowing sequentially per second is determined.

Here, the pressure controlling unit 20 includes: a connector 21 which connects the tubes with each other to provide a communicating space; a cover body 22 joined onto the connector to fix the position of a motor 23; a push rod 24 which is rotated or not according to the operation of the motor, has a rotational end portion with a screw thread and is fastened after vertically penetrating through a path formed from the motor to the tube 1; and a needle valve 25 geared through the screw thread of the push rod and turned upside down by rotation of the push rod by the motor so as to determine the degree of opening of the inner space of the tube 1.

The connector 21 means all kinds of connection means, and is mounted between the tubes to provide an inner communication space. Furthermore, the object of the present invention can be achieved through the connector which maximizes mutual connectability between the tube and the pressure controlling unit.

The motor 23 is means for controlling the push rod, is a motor moving at a predetermined angle in correspondence to the number of input pulses, and is also called a pulse motor or a step motor. The motor can more precisely control a rotational angle based on the property that the rotational angle of the motor is completely proportional to the number of input pulses.

As shown in the drawings, the push rod 24 induces interference to the flow of gas by opening or blocking the corresponding space according to operation of the motor if pressure control is needed for accordance with the supply amount while remaining in the space where gas flows.

That is, the push rod 24 is operated in such a way as to control the flow of gas within the gas flow space while being turned upside down as shown in FIGS. 3 and 4, thereby properly controlling the number of flows of bubbles per second as the user intends.

In the meantime, the present invention provides an improved and differentiated method for sensing and controlling an amount of gas supply using such an apparatus 100 for sensing and controlling an amount of gas supply.

Step 1

Sense bubbles of target gas, which flows from the bottom to the top in the tube 1, in real time by the sensing unit 10 having the optical sensor.

Step 2

Transmit flow information of the bubbles sensed by the sensing unit 10 to the controller in real time, and determine whether or not the flow information matches the predetermined supply amount of gas by the number of bubbles during any period of time.

Step 3

Transmit a command signal of the corresponding controller to the pressure controlling unit 20 in order to vary the number of bubbles based on the determined result and match the changed number of bubbles with the target supply amount of gas.

Step 4

Rotate the push rod 24 at an angle matching a correction value, which is reset based on the relevant information applied from the controller so that the needle valve 25 is turned upside down, and control the number of bubbles per second according to whether or not the inner space of the tube 1 is opened or blocked.

As described above, according to the present invention, the apparatus for sensing and controlling an amount of gas supply and the method for sensing and controlling an amount of gas supply thereby can sense the supply amount of the corresponding gas from the optical sensor in real time on the basis of the number of bubbles generated by any set time difference at the time when the target gas flows in the tube, thereby differentiating the supply amount more accurately and whether or not the gas supply state is bad. Particularly, the apparatus for sensing and controlling an amount of gas supply and the method for sensing and controlling an amount of gas supply thereby can control pressure of the tube in real time by a series of automated devices in order to precisely realize the target supply amount according to gas supply information obtained from the optical sensor, thereby positively preventing malfunction and continuously maintaining the initial set amount of gas supply.

As described above, while the present invention has been particularly shown and described with reference to the example embodiments thereof, it will be understood by those of ordinary skill in the art that the above embodiments of the present invention are all exemplified and various changes, modifications and equivalents may be made therein without changing the essential characteristics and scope of the present invention. Therefore, it would be understood that the embodiments disclosed in the present invention are not to limit the technical idea of the present invention but to describe the present invention, and the technical and protective scope of the present invention shall be defined by the illustrated embodiments. It should be also understood that the protective scope of the present invention is interpreted by the following claims and all technical ideas within the equivalent scope belong to the technical scope of the present invention.

The invention claimed is:

1. An apparatus for sensing and controlling an amount of gas supply, comprising:
    a tube for allowing a target gas to flow from a bottom to a top;
    a sensing unit engaged to an external surface of the tube to sense a number of bubbles of the target gas, which sequentially moves for a predetermined period of setting time in an inner space of the tube, in real time by applying an optical sensor based on signal information of a light emitting diode and a transistor, which are positioned to face each other;
    a controller for receiving bubble information from the sensing unit to determine whether the bubble information matches a target amount of gas supply in consideration of the predetermined period of setting time; and
    a pressure controlling unit which is operated by a signal obtained from the controller and varies the number of bubbles during a predetermined period of time by determining a degree of a blocked state of the inner space of the tube through a motor so as to match the varied number of bubbles to the target amount of gas supply.

2. The apparatus according to claim 1, wherein the tube comprises a first tube and a second tube, and the pressure controlling unit comprises:
    a connector which connects the first and second tubes with each other to provide a communicating space;
    a cover body joined onto the connector to fix a position of the motor;
    a push rod which is rotated or not rotated according to operation of the motor, has a rotational end portion with a screw thread and is fastened after vertically penetrating through a path formed from the motor to the tube; and
    a needle valve geared through the screw thread of the push rod and turned down by rotation of the push rod by the motor so as to determine a degree of opening of the inner space of the tube.

3. A method for sensing and controlling an amount of gas supply, comprising:
    a first step of sensing bubbles of a target gas, which flows from a bottom to a top in a tube, in real time by a sensing unit having an optical sensor;

a second step of transmitting flow information of the bubbles sensed by the sensing unit to a controller in real time, and determining whether or not the flow information matches a predetermined supply amount of gas by a number of bubbles during a period of time;

a third step of transmitting a command signal of the corresponding controller to a pressure controlling unit order to vary the number of bubbles based on a determined result and match a changed number of bubbles with a target supply amount of gas; and a fourth step of rotating a push rod at an angle matching a correction value, which is reset based on the relevant information applied from the controller, so that a needle valve is turned upside down, and controlling the number of bubbles per second according to whether or not an inner space of the tube is opened or blocked.

* * * * *